(12) United States Patent
Warren

(10) Patent No.: US 6,292,696 B1
(45) Date of Patent: *Sep. 18, 2001

(54) DEVICE AND METHOD PROVIDING ATRIAL ANTI-TACHYARRHYTHMIA THERAPY

(75) Inventor: Jay A. Warren, North Oaks, MN (US)

(73) Assignee: Cardiac Pacemakers, Inc., St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/558,937

(22) Filed: Apr. 26, 2000

Related U.S. Application Data

(62) Division of application No. 09/130,090, filed on Aug. 7, 1998, now Pat. No. 6,091,991.
(60) Provisional application No. 60/055,181, filed on Aug. 8, 1997.

(51) Int. Cl.[7] ................................................... A61N 1/362
(52) U.S. Cl. .................................................................. 607/14
(58) Field of Search ................................ 607/4, 5, 14, 15; 604/65

(56) References Cited

U.S. PATENT DOCUMENTS

| 3,939,844 | 2/1976 | Pequignot | 128/419 PG |
|---|---|---|---|
| 4,593,695 | 6/1986 | Wittkampf | 128/419 PG |
| 5,156,148 | 10/1992 | Cohen | 129/419 |
| 5,514,164 | 5/1996 | Mann et al. | 607/25 |
| 5,690,686 | 11/1997 | Min et al. | 607/5 |
| 5,792,183 | 8/1998 | Esler | 607/4 |
| 5,792,205 | 8/1998 | Alt et al. | 607/32 |
| 5,968,079 | 10/1999 | Warman et al. | 607/5 |

*Primary Examiner*—William E. Kamm
(74) *Attorney, Agent, or Firm*—Schwegman, Lundberg, Woessner & Kluth, P.A.

(57) ABSTRACT

Anti-tachyarrhythmia therapy, such as a countershock, is provided to an atrium needing treatment, but delays its delivery for a programmable period of time following an indication of susceptibility to ventricular tachyarrhythmia (VT). This reduces the risk of reinducing VT during a period in which the heart is abnormally metabolically vulnerable to VT, including ventricular fibrillation (VF). The delay time may be independently programmed for different indications of VT, and may be synchronized to and delayed from the R-wave. The delay time may be adjusted, such as to exceed one second, or even to exceed several hours, in order to accommodate the metabolic abnormal susceptibility of the particular patient in the wide range of patients needing treatment of atrial tachyarrhythmias.

26 Claims, 6 Drawing Sheets

DEVICE AND METHOD PROVIDING ATRIAL ANTI-TACHYARRHYTHMIA THERAPY

This application is a Division of U.S. application Ser. No. 09/130,090 filed on Aug. 7, 1998, now U.S. Pat. No. 6,091,991, which claims the benefit under 35 U.S.C. § 119(e) of U.S. Provisional Application No. 60/055,181, filed on Aug. 8, 1997, the specifications of which are hereby incorporated by reference.

TECHNICAL FIELD OF THE INVENTION

This invention relates generally to cardiac rhythm management devices and methods, and more particularly to an implantable device, such as a cardioverter-defibrillator, and method for treating atrial tachyarrhythmias.

BACKGROUND OF THE INVENTION

Atria tachyarrhythmias are quite common, and are seen even in patients who are not acutely ill. One such atrial tachyarrhythmia, atrial fibrillation, does not usually pose an immediate threat to the patient's life, but prolonged atrial fibrillation can compromise patient hemodynamics. Inadequate blood flow due to atrial fibrillation may lead to blood clots, which increase the risk of strokes. Other symptoms may include palpitations of the heart, dizziness, or loss of consciousness.

One method of treating atrial fibrillation is to deliver a countershock to terminate the arrhythmia. For example, the countershock may be applied via an external or implantable defibrillator. However, this method of treating atrial fibrillation risk causing ventricular tachyarrhythmias, including life-threatening ventricular fibrilation.

One method of reducing the risk of ventricular fibrillation is by synchronizing the delivery of a countershock to an electrical ventricular activation (R-wave) of the heart. There is, however, a need in the art to further reduce the risk of inducing ventricular tachyarrhythmias, such as life-threatening ventricular fibrilion, during the countershock treatment of comparatively less exigent atrial tachyarrhythmias.

SUMMARY OF THE INVENTION

The present invention provides a method of applying anti-tachyarrhythmia therapy, such as a countershock, to the heart. From the atrium of the heart, atrial activity needing anti-tachyarrhythmia therapy is detected. Ventricular activity is monitored for an indication of abnormal susceptibility to ventricular tachyarrhythmia. Anti-tachyarrhythmia therapy is delivered to the atrium in response to the detected atrial tachyarrhythmia activity. But the atrial tachyarrhythmia therapy is delayed for a first time delay if the indication of abnormal susceptibility to ventricular tachyarrhythmia is detected.

The present invention also provides an device, such as an implantable cardioverter-defibrillator, for delivering anti-tachyanhythmia therapy to the heart. An atrial receiver receives an atrial heart activity signal from an atrium of the heart. A ventricular receiver receives a ventricular heart activity signal from the ventricle of the heart. A controller controls the delivery of the anti-tachyarrhythmia therapy to the atrium in response to the atrial heart activity signal indicating a need for the anti-tachyarrhythmia therapy. The controller includes a first timer for delaying the delivery, by a first time delay, of the anti-tachyarrhythmia therapy to the atrium in response to the ventricular heart activity signal indicating abnormal susceptibility to a ventricular tachyarrhythmia.

In one embodiment, the countershock or other anti-tachyarrhythrnia therapy is synchronized to or delayed from the R-wave. In another embodiment, following the indication of abnormal susceptibility to a ventricular tachyarrhythmia, the first timer is reset and the value of the first time delay is adjusted according to the particular type of indication of abnormal susceptibility to a ventricular tachyarrhythmia. The value of the first time delay can be programmed depending on the patient's vulnerability to ventricular tachyarrhythmia. The delay can be programmed to exceed approximately one second or approximately several hours. In one embodiment, the first timer is reset and the value of the first time delay is adjusted subsequent to delivery of an atrial countershock.

The present invention delays delivery of atrial anti-tachyarrhythmia therapy when an indication of abnormal susceptibility to a ventricular tachyarrhythmia is present. As a result, the present invention reduces the risk of reinducing ventricular tachyarrhythmias, such as life-threatening ventricular fibrillation, which can be caused by the delivery of anti-tachyarrhytmia therapy to the atrium.

BRIEF DESCRIPTION OF THE DRAWINGS

In the drawings, like numerals describe substantially similar components throughout the several views.

DETAILED DESCRIPTION OF THE INVENTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents.

The present invention provides anti-tachyarrhythmia therapy to an atrium of a heart. In this application, atrial tachyarrhytmias (ATs) are understood to comprise any atrial tachyarrhythmia including, but not limited to: sinus tachycardia, atrial flutter, atrial tachycardia, atrial fibrillation, AV nodal reentrant tachycardia. Ventricular tachyarrhythmias (VTs) are understood to comprise any ventricular tachyarrhythmia including, but not limited to, ventricular fibrillation (VF). Cardioversion and defibrillation are understood to refer generally to any treatment of a cardiac arrhythmia by an electrical countershock. Cardioverter and defibrillator are understood to refer generally to any device capable of treating a cardiac arrhythmia through an electrical countershock. Anti-tachyarrhythmia therapy is understood to comprise treatment of atrial tachyarrhythmia by electrical countershock, anti-tachyarrhythmia drugs, or anti-tachycardia pacing.

The present invention provides anti-tachyarrhythmia therapy, such as countershock therapy, to the atrium of the heart such that the risk of ventricular tachyarrhythmias, particularly that of life-threatening ventricular fibrillation, is minimized. As described in detail below, the present invention recognizes time periods in which the ventricle of the heart may be abnormally susceptible to ventricular tachyarrhythmias, and avoids treatment of atrial tachyarrhythmias during these vulnerable periods.

Figure 1:
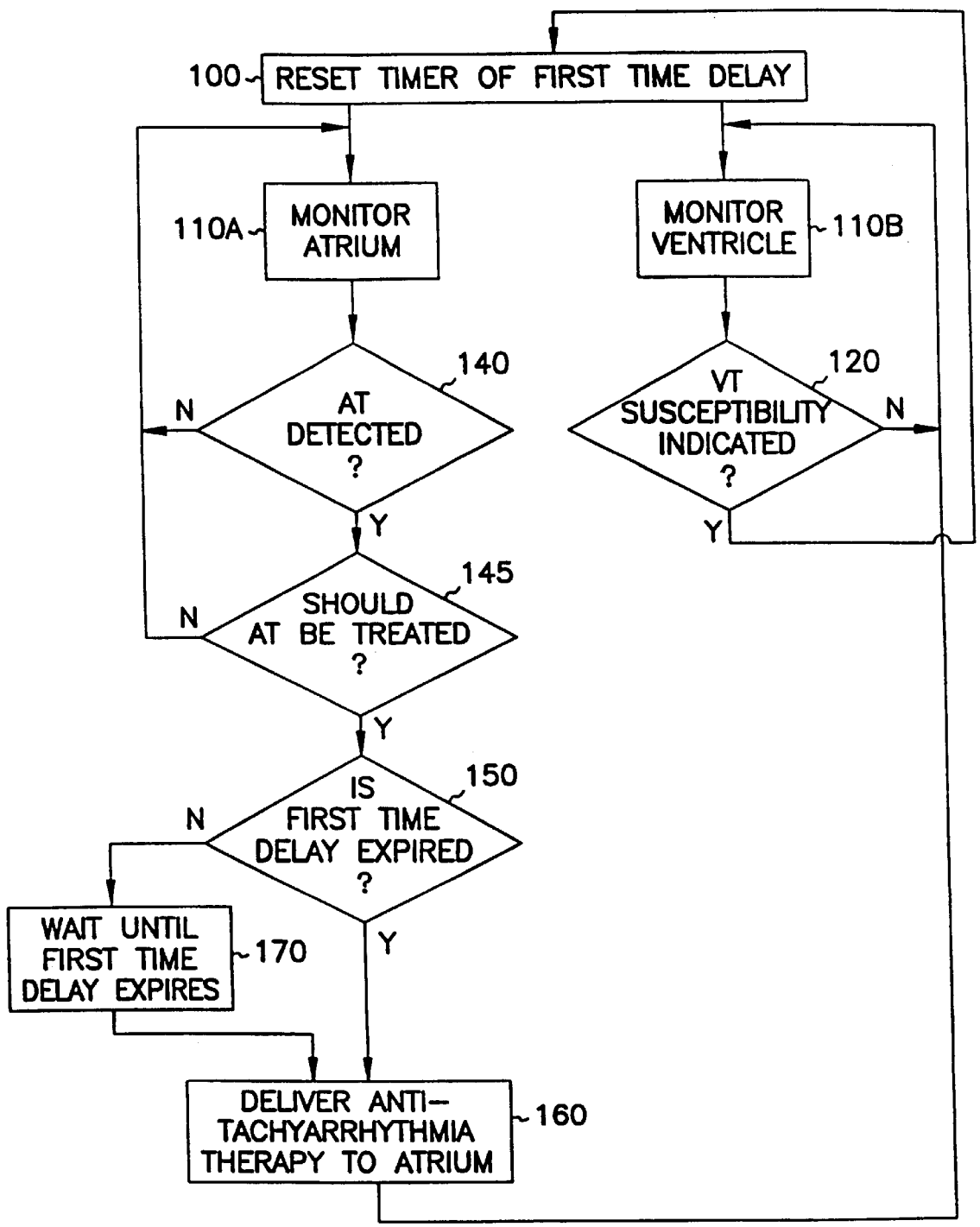
FIG. 1 is a flow chart illustrating one embodiment of a method of delivering an atrial countershock to treat tachyarrhythmias.

FIG. 1 is a flow chart illustrating one embodiment of the method according to the present invention. In FIG. 1, a first timer for measuring a first time delay is initially reset at step 100. An atrium of the heart and a ventricle of the heart are concurrently and continuously monitored at steps 110A–B. The atrium is monitored for any atrial tachyarrhythnia activity needing anti-tachyarrhythmia therapy, such as atrial fibrillation. The ventricle is monitored for any ventricular vulnerability, i.e. any indication of abnormal susceptibility to a ventricular tachyarrhythmia (VT), and particularly for abnormal susceptibility to ventricular fibrillation (VF). Sensed electrical indications of abnormal susceptibility to a ventricular tachyarrhythmia may include, but are not limited to: one or more premature ventricular contractions (PVCs); a particular number of premature ventricular contractions detected during a particular third period of time, such as, for example, 6 to 8 premature ventricular contractions occurring within an hour; a particular number of successive premature ventricular contractions; ventricular tachycardia bigeminy; non-sustained monomorphic or polymorphic ventricular tachycardia; sustained monomorphic or polymorphic ventricular tachycardia; and, ventricular fibrillation.

Indications of ventricular abnormal susceptibility are understood to include actual instances of ventricular tachyarrhythria, including ventricular fibrillation, and any other indication of abnormal susceptibility to ventricular tachywithythmia. For example, other suitable indications of abnormal susceptibility to ventricular tachyarrhythmia may include chemical or other indications. In one embodiment of the present invention, the actual delivery of atrial anti-tachyarrhythmia therapy, such as a countershock, is itself defined as an indication of abnormal susceptibility to ventricular tachyarrhythmia.

Indications of abnormal susceptibility to ventricular tachyarrhythmia are understood not to include the T-wave time periods within a cardiac cycle during which the heart is normally particularly vulnerable to an external stimulus. However, in one embodiment of the present invention that is described below, such normal time periods of vulnerability are also avoided by the present invention. It is also understood that the indications of abnormal susceptibility to ventricular tachyarrhythmia are programmably adjustable by the physician. Thus, those indications of susceptibility to ventricular tachyarrhythmia that are considered abnormal may vary from patient to patient.

One aspect of the present invention, is the recognition that such indications of abnormal susceptibility to ventricular tachyarrhythmia define time periods in which the heart is metabolically abnormally susceptible to induction of ventricular tachyarrhythmias, including life-threatening ventricular fibrillation. As described in detail below, the present invention avoids delivering anti-tachyarrhythmia, therapy, such as countershock treatment, to the atrium during these vulnerable time periods.

At step 120, if the ongoing ventricular monitoring of step 110B provides no indication of abnormal susceptibility to ventricular tachyarrhytmia, the ongoing monitoring of the atrium and ventricle continues at concurrent steps 110A–B. However, if abnormal susceptibility to ventricular tachyarrhythmia is indicated at step 120, the first timer for measuring the first time delay is reset at step 100 before the ongoing monitoring of the atrium and ventricle continues at concurrent steps 110A–B. Thus, the first timer measures the elapsed time from the last indication of ventricular tachyarrhythmia, if any.

Similarly, at step 140 if the ongoing atrial monitoring of step 110A provides no indication of a detected atrial tachyarrhythmia, the ongoing monitoring of the atrium and ventricle continues at concurrent steps 110A–B. When, at step 140, the atrial monitoring indicates detection of an atrial tachyarrhythmia, the present invention is typically capable of recognizing and distinguishing, at step 145, between different forms of atdal tachyarrhythmia detected at step 140, such that anti-tachyarrhythmia therapy is only delivered in response to particular forms of atrial tachyarrhythmia, e.g. atrial fibrillation (AF), as described below. If the detected atrial tachyarrhythmia does not indicate, at step 145, that anti-tachyarrhythmia therapy should be delivered, the monitoring of the atrium and ventricle is continued at concurrent steps 110A–B.

If, at step 145, the detected atrial tachyarrhythmia indicates that anti-tachyarrhythmia therapy should be delivered, the first timer for measuring the first time delay is checked at step 150. If the first time delay is expired (i.e., if the first timer's measurement of the elapsed time from the last indication of abnormal susceptibility to ventricular tachyarrhythmia, if any, exceeds the programmably adjustable value of the first time delay), a countershock or other anti-tachyarrhythmia therapy is delivered at step 160 to the atrium in which the atrial tachyarrhythmia was detected.

If, however, the first time delay has not expired (i.e., if the first timer's measurement of the elapsed time from the last indication of abnormal susceptibility to ventricular tachyarrhythmia, if any, does not exceed the programmably adjustable value of the first time delay), anti-tachyarrhythmia therapy is delayed at step 170 until the first time delay has expired. At step 170, after the first time delaly expires, the countershock or other anti-tachyarrhythmia therapy is delivered to the atrium at step 160. In this embodiment, the ongoing monitoring of the atrium and the ventricle may be optionally blanked during delivery of the anti-tachyarrhythmia therapy at step 110, but the ongoing monitoring continues following the delivery of the anti-tachyarrhythmia therapy to the atrium at step 160.

As set forth above, the first time delay is typically prograrnmably adjusted by the physician to accommodate the individual degree of metabolic vulnerability of the patient to ventricular tachyarrhythmia, including ventricular fibrillation. In the diverse patient population that is susceptible to atrial tachyarrhythmia, the metabolic vulnerability of the particular patient to ventricular tachyarrhythmia, including ventricular fibrillation, will vary widely. Thus, the duration of the first time delay, which follows the above-described indications of abnormal susceptibility to ventricular tachyarrhythmia, will also vary widely to accommodate this variability in the patient population.

The period of metabolic vulnerability that the first time delay should exceed is typically longer than the duration of a cardiac cycle, i.e. time between successive heartbeats. Therefore, the first time delay is typically adjustably programmed to a value exceeding one second. The first time delay may even be programmed to exceed one hour or several hours for patients that are abnormally metabolically vulnerable to ventricular tachyarrhythmia, such as ventricular fibrillation, following recent indications of abnormal susceptibility to ventricular tachyarrhythmia.

Figure 2:
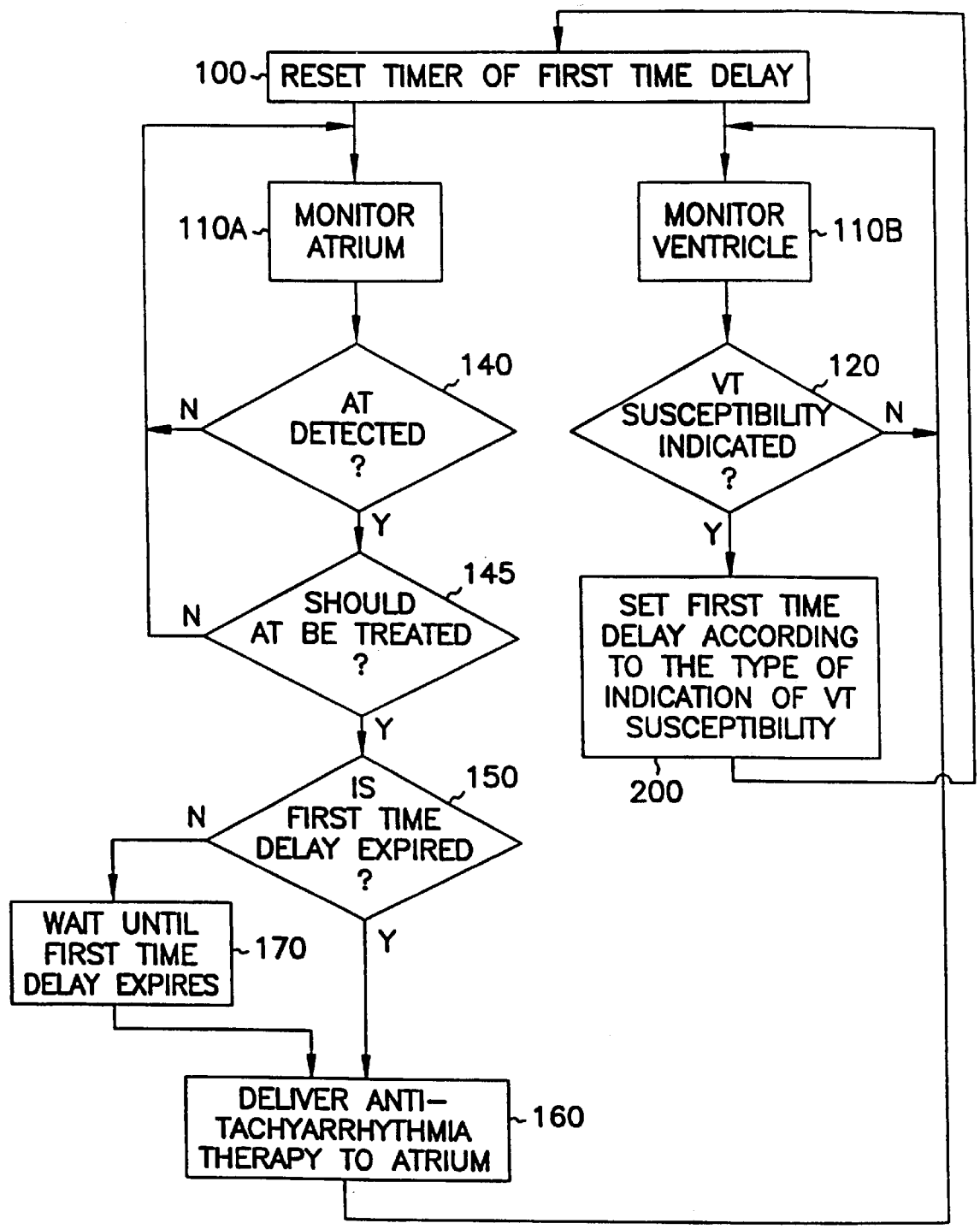
FIG. 2 is a flow chart illustrating an alternate embodiment of the method illustrated in FIG. 1, in which a first time delay is adjusted according to a type of indication of abnormal susceptibility to ventricular tachyarrhythmia.

FIG. 2 is a flow chart illustrating one embodiment of the present invention in which the duration of the first time delay depends on the particular type of one or more recent particular indications of abnormal susceptibility to ventricular tachyarrhythmia This embodiment allows the physician to independently program different values of the first time delay to correspond respectively to different types of indications of abnormal susceptibility to ventricular tachyarrhythmia For example, one indication of abnormal susceptibility to ventricular tachyarrhythmia may be a single premature ventricular contraction, for which the physician may program a corresponding first time delay to be several seconds. Another indication of abnormal susceptibility to ventricular tachyarrhythmia may be an actual episode of ventricular fibrillation, for which the physician may program a corresponding first time delay to be several hours.

The method illustrated in FIG. 2 closely follows that illustrated and described above with respect to FIG. 1, and like blocks or steps are indicated by the like numbers. However, in FIG. 2 at step 200, the invention recognizes the type of the most recent indication of abnormal susceptibility to ventricular tachyarrhythmia, and sets the value of the first time delay accordingly, unless doing so would cut short an unexpired longer first time delay corresponding to a previous indication of abnormal susceptibility to ventricular tachyarrhythmia. The invention then resets the first timer at step 100 before continuing the ongoing monitoring of the atrium and the ventricle at concurrent steps 110A–B.

Figure 3:
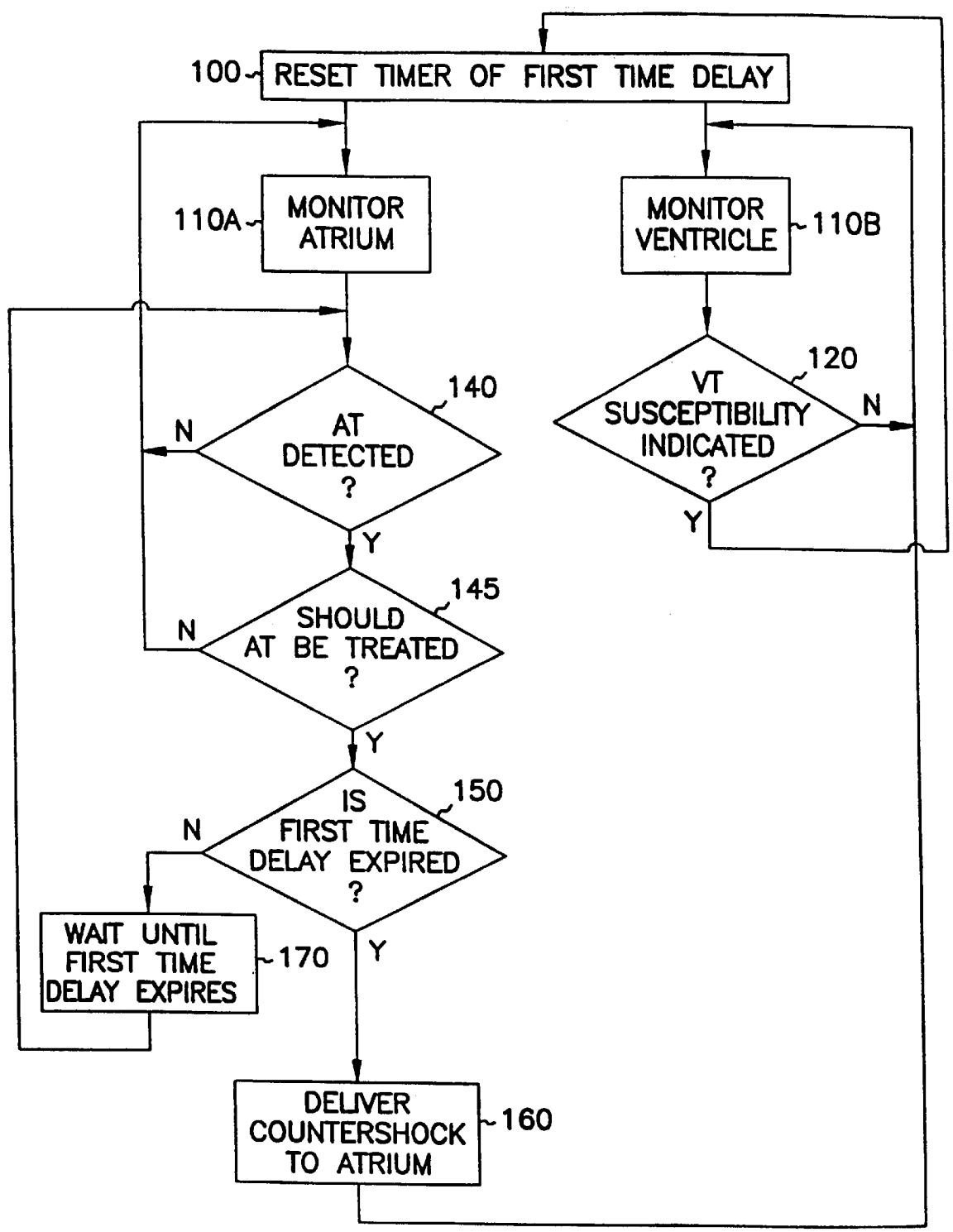
FIG. 3 is a flow chart illustrating an alternate embodiment of the method illustrated in FIG. 1 that rechecks for atrial tachyarrhythmia after waiting until a first time delay expires.

FIG. 3 is a flow chart illustrating an alternate embodiment of the method according to the present invention. The method illustrated in FIG. 3 closely follows that illustrated and described above with respect to FIG. 1, and like blocks or steps are indicated by the like numbers. However, in FIG. 3, after waiting until the first time delay expires at step 170, the present invention rechecks whether atrial tachyarrhythmia is detected at step 140. If atrial tachyarrhythmia is not present at step 140, or is determined at step 145 to be of a type not requiring treatment, the ongoing monitoring of the atrium and the ventricle is resumed at concurrent steps 110A–B. If atrial tachyarrhythmia is still present at step 140, and is determined at step 145 to be of a type requiring treatment, the invention finds the first time delay to be expired at step 150, and proceeds to deliver anti-tachyarrhythmia therapy, such as a countershock, to the atrium at step 160.

Figure 4:
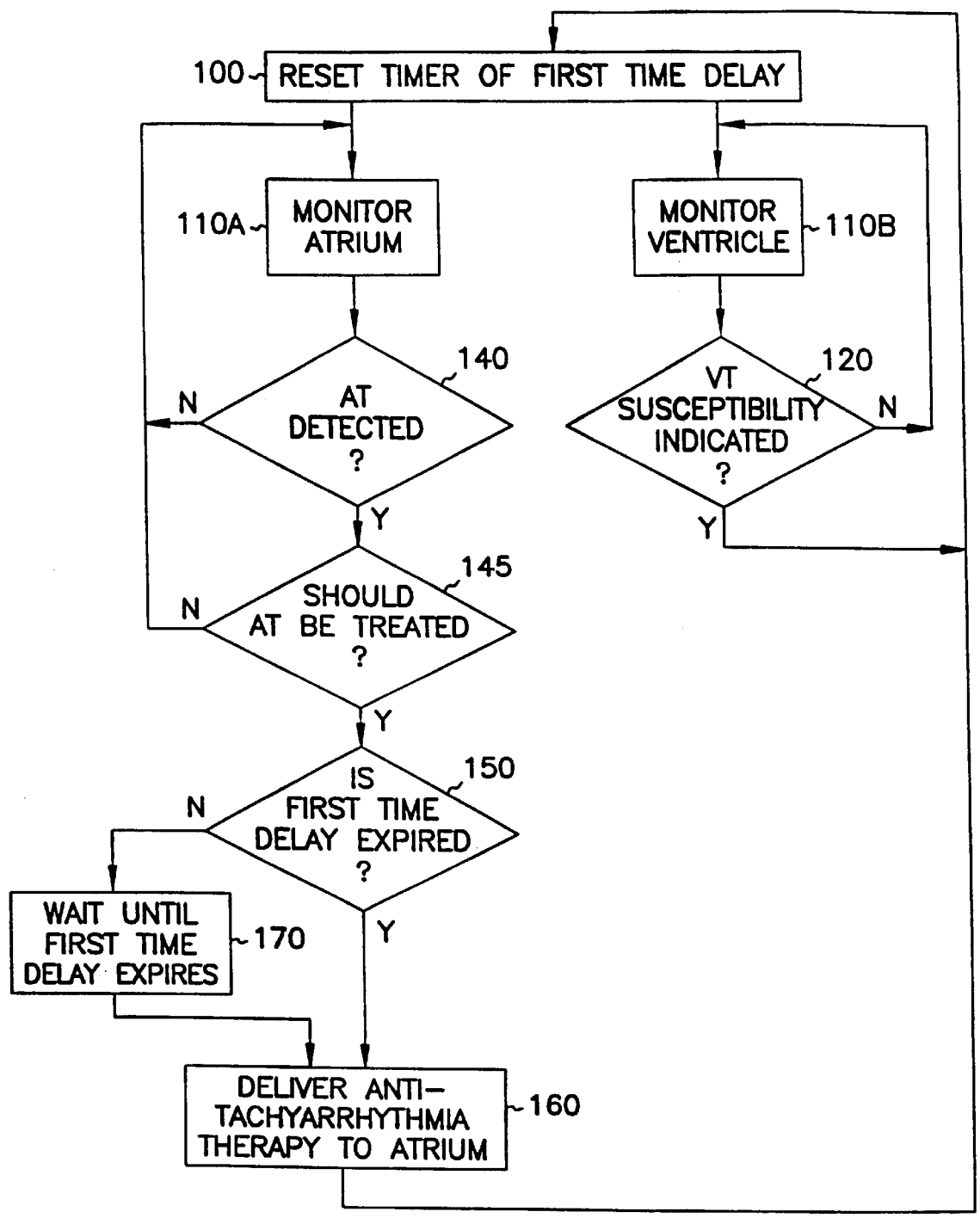
FIG. 4 is a flow chart illustrating an alternate embodiment of the method illustrated in FIG. 1, in which a first timer is reset after delivery of anti-tachyarrhythmia therapy to the atrium.

FIG. 4 is a flow chart illustrating an alternate embodiment of the method according to the present invention. The method illustrated in FIG. 4 closely follows that illustrated and described above with respect to FIG. 1, and like blocks or steps are indicated by the like numbers. However, in FIG. 4, after the anti-tachyarrhythmia therapy, such as a countershock, is delivered to the atrium at step 160, the timer for measuring the first time delay is reset at step 100 before the ongoing monitoring of the atrium and ventricle continues at concurrent steps 110A–B. Thus, according to the method illustrated in FIG. 4, subsequent atrial anti-tachyarrhythmia therapy is delayed by at least the first time delay regardless of whether or not ventricular tachyarrhythmia is indicated at step 120. By contrast, according to the embodiment illustrated in FIG. 1, subsequent atrial anti-tachyarrhythmia therapy can be delivered immediately, i.e. without waiting for the duration of first time delay, if ventricular tachyarrhythmia is not indicated subsequent to a first delivery of atrial anti-tachyarrhythmia therapy.

Figure 5:
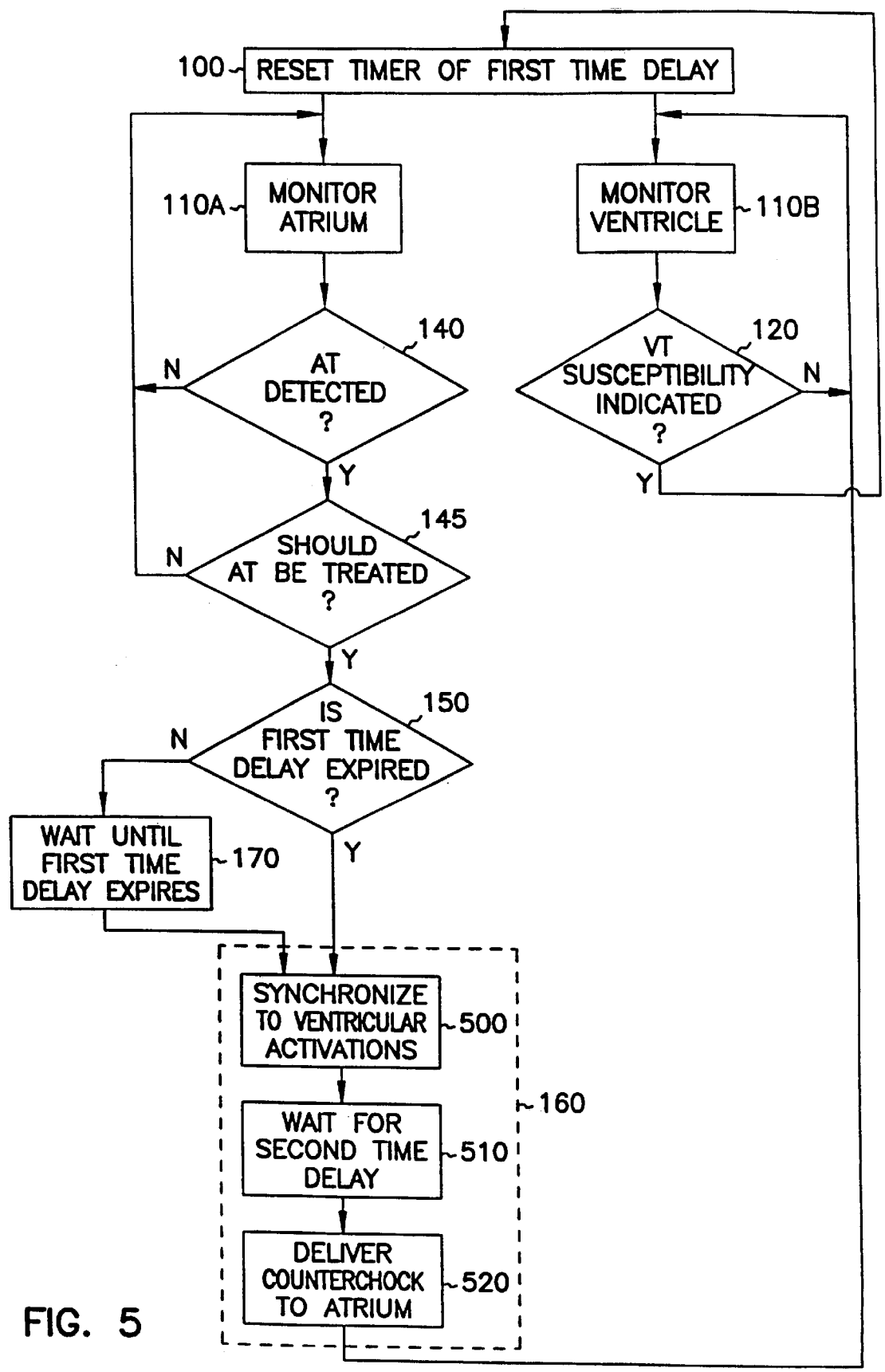
FIG. 5 is a flow chart illustrating, in more detail, one embodiment of the step of delivering the atrial anti-tachyarrhythmia therapy in FIGS. 1–4.

In FIGS. 1–4, delivery of the atrial anti-tachyarrhythmia therapy, such as a countershock, at step 160 typically includes synchronizing the delivery to ventricular activations (R-waves) of the heart FIG. 5 is a flow chart illustrating, by way of example, one embodiment of the details of step 160 in more detail. The method illustrated in FIG. 5 closely follows that illustrated and described above with respect to FIG. 1, and like blocks or steps are indicated by the like numbers. However, the additional details of step 160 that are illustrated in FIG. 5 may also be applicable to other embodiments of the present invention, such as those illustrated in FIGS. 1–4.

In FIG. 5, delivery of anti-tachyarrhythmia therapy at step 160 includes synchronizing to one of the ventricular activations (R-waves) of the heart at step 500. Such ventricular activations are detected during the ongoing monitoring of the ventricle at step 110B. Synchronizing the delivery of the anti-tachyarrhythmia therapy to one of the ventricular activations reduces the risk of delivering a countershock to the heart during the T-wave period in a cardiac cycle in which the heart is particularly vulnerable to induction of ventricular fibrillation. At step 510, an optional second time delay is provided to offset in time from the R-wave the delivery of the anti-tachyarrhythmia therapy. In one embodiment, the second time delay is shorter than the approximately 250 millisecond interval between the R-wave and the T-wave that immediately follows. The anti-tachyarrhythmia therapy, such as a countershock, is delivered to the atrium at step 520 after the second time delay has expired. In this embodiment, the anti-tachyarrhythmia therapy comprises a countershock delivered synchronously to and optionally delayed from the ventricular activation (R-wave), such that the atrial countershock is delivered between an R-wave and a T-wave.

Figure 6:
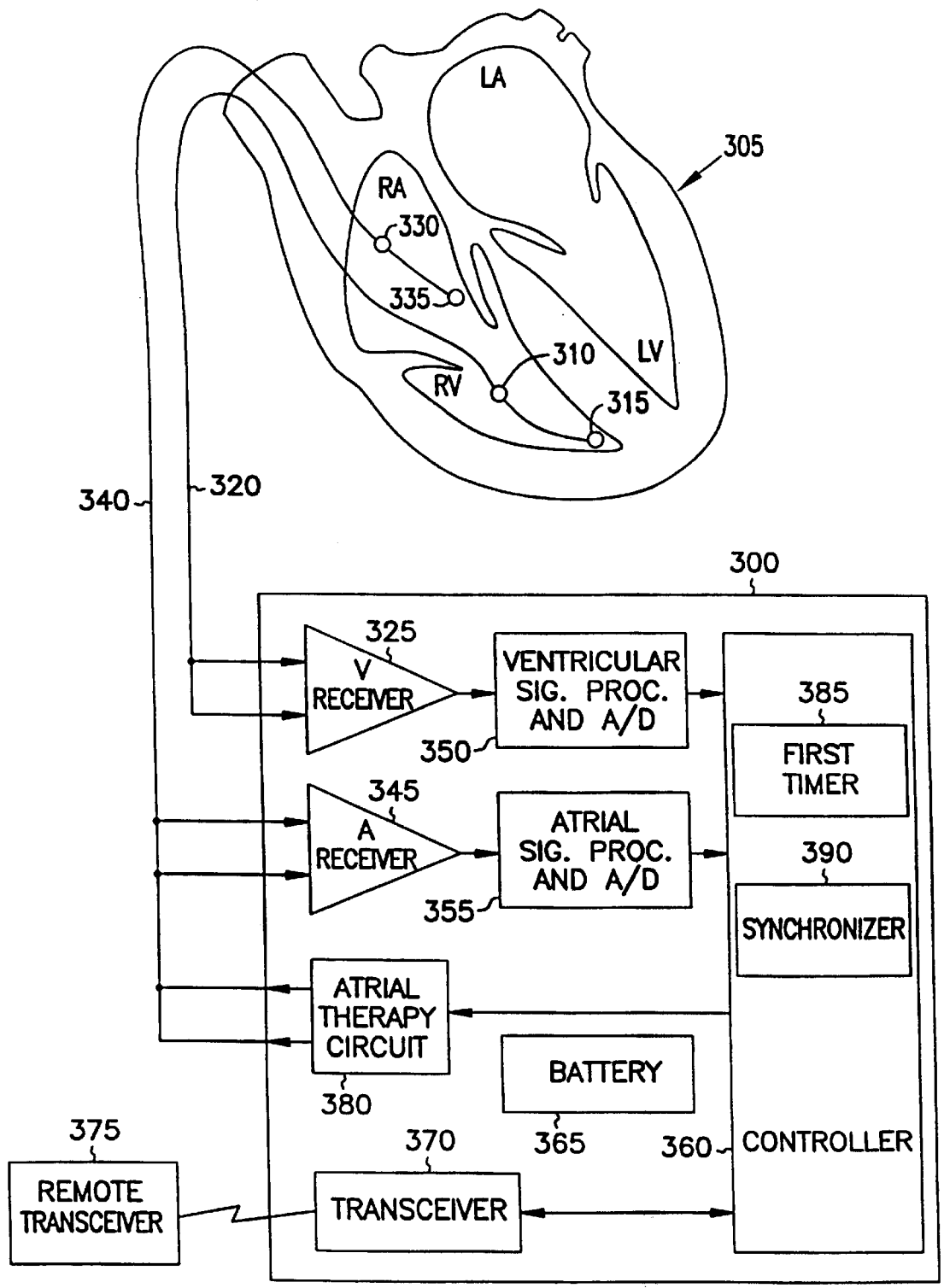
FIG. 6 is a schematic diagram illustrating one embodiment of the present invention in relation to a heart to which it delivers therapy.

FIG. 6 is a schematic illustration of one embodiment of an implantable device, such as implantable cardioverter-defibrillator 300, for delivering anti-tachyarrhythmia therapy according to the present invention. Cardioverter-defbrillator 300 is illustrated in relation to a heart 305 to which it delivers therapy. Ventricular heart activity is sensed by a ventricular sensor such as electrodes 310 and 315, which are independently electrically coupled through ventricular lead 320 to ventricular receiver 325 in cardioverter-defibriflator 300. Atrial heart activity is sensed by an atrial sensor, such as atrial electrodes 330 and 335, which are independently electrically coupled through atrial lead 340 to atrial receiver 345 in cardioverter-defibrillator 300.

For the embodiment of the cardioverter-defibrillator 300 illustrated in FIG. 6, the received ventricular and atrial signals may undergo further signal processing, including amplification, analog filtering, and analog-to-digital conversion in respective ventricular and atrial signal processing channels 350 and 355 before being provided to a controller 360. Controller 360 typically includes a microprocessor and associated interface circuitry. Cardioverter-defibrillator 300 also includes: a battery 365, for providing power to its various electrical components; transceiver 370, for communication with external remote transceiver 375; atrial therapy circuit 380, for providing anti-tachyarrhythmia therapy, such as an electrical countershock pulse, to the atrium of the heart 305. Atrial lead 340 and atrial electrodes 330 and 335 are also electrically coupled to cardioverter-defibrillator 300 for delivery of the anti-tachyarrhythmia therapy from cardioverter-defibrillator 300 to the atrium of the heart 305.

Controller 360 is capable of detecting and distinguishing between the indications of ventricular tachyarrhythrnia, as described above with respect to FIG. 1. Controller 360 is also capable of detecting the ventricular activatiois (R-waves) of the heart 305, as described above with respect to FIG. 5. Controller 360 is also capable of detecting atrial activity and distinguishing between atrial tachyarrhythmia activity needing anti-tachyarrhythmia therapy, such as atrial fibrillation, and atrial tachyarrhythmia activity not requiring anti-tachyarrhythmia therapy. Controller 360 also includes a first timer 385 for measuring an elapsed time from an indication of abnormal susceptibility to ventricular tachyarrhythmia The elapsed time of first timer 385 is compared to a first time delay value that is externally adjustably programmable from remote transceiver 375 through transceiver 370.

First timer 385 may be an analog timer or digital counter, or a software timer, or any other suitable timer implementation. The value of the first time delay is adjustably programmed by the physician to exceed the estimated time period of metabolic vulnerability for a patient following a recent indication of abnormal susceptibility to ventricular tachyarrhythmia. First timer 385 is reset at each indication of abnormal susceptibility to ventricular tachyarrhythmia, and in one embodiment, the first time delay is also adjusted to correspond to a value that is particularized to each type of indication of ventricular tachyarrhythmia, as described above with respect to FIG. 2.

When controller 360 detects an atrial tachyarrhythmia needing therapy, it provides anti-tachyarrhythmia therapy, such as a countershock, through retrial therapy circuit 380, to the atrium when a sufficient time has elapsed since the last indication of abnormal susceptibility to ventricular tachyarrhytmia (i.e., when first timer 385 indicates that the first time delay has expired). If, upon detection of the atrial tachyarrhythmia, the first time delay has not expired, controller 360 waits until the first time delay 385 has expired. In one embodiment, controller 360 rechecks whether atrial tachyarrhythmia is still present, after waiting until the first time delay 385 has expired, before delivering anti-tachyarrhythmia therapy to the atrium, as described above with respect to FIG. 3. In another embodiment, controller 360 is immediately capable of delivering subsequent atrial anti-tachyarrhythrrua therapy, as described above with respect to FIGS. 1–2. In another embodiment, controller 360 resets first timer 385 after atrial anti-tachyarrhythmia therapy is delivered, such that subsequent atrial anti-tachyarrhythnia therapy is inhibited for a corresponding period of time, as described above with respect to FIG. 4. In one embodiment, delivery of atrial anti-tachyarrhythmia therapy is itself defined as an indication of abnormal susceptibility to ventricular tachyarrhythmia having a separate corresponding first time delay value. In this embodiment, after delivery of atrial anti-tachyarrhythmia therapy, controller 360 adjusts the first time delay accordingly, as described above with respect to FIG. 2.

Controller 360 typically also includes synchronizer 390 for synchronizing delivery of the atrial anti-tachyarrhythmia therapy to a ventricular activation (R-wave) sensed by ventricular receiver 325, as described above with respect to FIG. 5. In one embodiment, synchronizer 390 includes a second timer for delaying the synchronous delivery of the atrial anti-tachyarrhythmia therapy for a second time delay, as described above with respect to FIG. 5.

Thus, the present invention provides anti-tachyarrhythmia therapy to the atrium of the heart such that the risk of ventricular tachyarrhythmias, particularly that of life-threatening ventricular fibrillation, is minimized. The present invention recognizes that the heart is metabolically abnormally susceptible to reinduction of ventricular tachyarrhythmias during the time periods that follow indications of abnormal susceptibility to ventricular tachyarrhythmias. The present invention avoids atrial anti-tachyarrhythmia therapy, such as countershock treatment, during these vulnerable periods, thereby reducing the risk of inducing ventricular fibrillation.

It should be understood that the present invention may be implemented, for example, in a cardioverter-defibrillator that provides anti-tachyarrhythnia therapy, such as a countershock, to the atrium only. The present invention may also be implemented as part of a dual-chamber cardioverter-defibrillator that provides anti-tachyarrhythmia therapy, such as a countershock, to both the atrium and ventricle. Also, the anti-tachyarrhythmia therapy may also include therapy other than countershocks without departing from the scope and spirit of the present invention. For example, anti-tachycardia pacing or drug delivery therapy could be similarly delayed from the above-described indications of ventricular tachyarrhythmias. In another example, bradycardia pacing therapy could be combined with the above-described functionality of the present invention.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. An implantable device for delivering anti-tachyarrhythmia therapy to a heart, the device comprising:
   an atrial receiver for receiving an atrial heart activity signal from an atrium of the heart;
   a ventricular receiver for receiving a ventricular heart activity signal from a ventricle of the heart;
   an atrial therapy circuit for delivering anti-tachyarrhythmia therapy to the atrium; and
   a controller, coupled to each of the atrial therapy circuit and the atrial and ventricular receivers, for controlling the delivery of the anti-tachyarrhythmia therapy to the atrium in response to the atrial heart activity signal indicating a need for anti-tachyarrhythmia therapy, and wherein the controller includes a first timer for delaying, for a first time delay, the delivery of the anti-tachyarrhythmia therapy to the atrium by a first time delay in response to the ventricular heart activity signal that includes an indication of abnormal susceptibility to a ventricular tachyarrhythmia.

2. The device of claim 1, wherein the anti-tachyarrhythmia therapy includes an electrical countershock.

3. The device of claim 1, wherein the anti-tachyarrhythmia therapy includes delivery of an anti-tachyarrhythmia drug.

4. The device of claim 1, wherein the anti-tachyarrhythmia therapy includes anti-tachycardia pacing.

5. The device of claim 1, wherein the controller includes a synchronizer for synchronizing the delivery of the anti-tachyarrhythmia therapy to the ventricular heart activity signal indicating a ventricular activation.

6. The device of claim 5, wherein the controller includes a second timer for delaying the delivery of the anti-tachyarrhythmia therapy, for a second time delay, from the ventricular activation to which it is synchronized.

7. The device of claim 6, wherein the second time delay is shorter than an interval between the ventricular activation to which the anti-tachyarrhythmia therapy is synchronized and a T-wave immediately following the ventricular activation to which the anti-tachyarrhythmia therapy is synchronized.

8. The device of claim 1, wherein the first time delay exceeds approximately one second.

9. The device of claim 1, wherein the first time delay exceeds approximately one hour.

10. The device of claim 1, wherein the first time delay exceeds approximately several hours.

11. The device of claim 1, wherein the first time delay exceeds a period in which the ventricle is abnormally susceptible to tachyarrhythmia from the anti-tachyarrhythmia therapy applied to the atrium.

12. The device of claim 1, wherein the first time delay is adjustable.

13. The device of claim 12, wherein the first time delay is programmable based upon an abnormal susceptibility of an individual patient to ventricular tachyarrhythmia in response to the anti-tachyarrhythmia therapy applied to the atrium.

14. The device of claim 1, wherein the first time delay depends on the type of the indication of abnormal susceptibility to the ventricular tachyarrhythmia.

15. The device of claim 1, wherein the first time delay is adjusted subsequent to the delivery of the anti-tachyarrhythmia therapy to the atrium.

16. The device of claim 1, wherein the indication of abnormal susceptibility to the ventricular tachyarrhythmia includes at least one premature ventricular contraction.

17. The device of claim 16, wherein the indication of abnormal susceptibility to the ventricular tachyarrhytmia includes at number of premature ventricular contractions detected over a third period of time.

18. The device of claim 16, wherein the indication of abnormal susceptibility to the ventricular tachyarrhythmia includes a number of successive premature ventricular contractions.

19. The device of claim 1, wherein the indication of abnormal susceptibility to the ventricular tachyarrhythmia includes a non-sustained ventricular tachycardia.

20. The device of claim 1, wherein the indication of abnormal susceptibility to the ventricular tachyarrhythmia includes a ventricular tachycardia.

21. The device of claim 1, wherein the indication of abnormal susceptibility to the ventricular tachyarrhythmia includes a ventricular fibrillation.

22. The device of claim 1, wherein the indication of abnormal susceptibility to the ventricular tachyarrhythmia is chemical.

23. The device of claim 1, wherein the indication of abnormal susceptibility to the ventricular tachyarrhythmia is anti-tachyarrhythmia therapy that was previously delivered to the heart.

24. The device of claim 1, further comprising:
   an atrial sensor for detecting the atrial heart activity signal;
   a ventricular sensor for detecting the ventricular heart activity signal;
   an atrial lead for coupling the atrial sensor to the atrial receiver; and
   a ventricular lead for coupling the ventricular sensor to the ventricular receiver.

25. The device of claim 24, wherein the atrial sensor comprises a pair of electrodes for detecting the atrial heart activity signal and for coupling the anti-tachyarrhythmia therapy to the atrium.

26. The device of claim 24, wherein the ventricular sensor comprises a pair of electrodes for detecting the ventricular heart activity signal.

* * * * *